(12) United States Patent
McDonald et al.

(10) Patent No.: US 12,338,059 B2
(45) Date of Patent: Jun. 24, 2025

(54) APPARATUS, SYSTEM AND METHOD COMPRISING A DISPENSER WITH A MODULAR CARTRIDGE FOR THE DISPENSING OF CANNABIS EXTRACT

(71) Applicant: Jetty Marketing, LLC, Oakland, CA (US)

(72) Inventors: Michael James McDonald, Lafayette, CA (US); Robert William Ferguson, Oakland, CA (US); Ron Abraham Gershoni, Oakland, CA (US); Nathan Charles Ferguson, Oakland, CA (US); Katherine Alexander McWilliams, Carlsbad, CA (US); Ryan Artale, Crested Butte, CO (US)

(73) Assignee: Jetty Marketing, LLC, Oakland, CA (US)

( * ) Notice: Subject to any disclaimer, the term of this patent is extended or adjusted under 35 U.S.C. 154(b) by 276 days.

(21) Appl. No.: 17/819,694

(22) Filed: Aug. 15, 2022

(65) Prior Publication Data

US 2023/0048464 A1 Feb. 16, 2023

Related U.S. Application Data

(60) Provisional application No. 63/232,768, filed on Aug. 13, 2021.

(51) Int. Cl.
*B65D 83/00* (2006.01)
*A24F 42/00* (2020.01)
*B65D 83/761* (2025.01)

(52) U.S. Cl.
CPC ...... *B65D 83/761* (2025.01); *B65D 2583/005* (2013.01)

(58) Field of Classification Search
CPC . B05C 17/00533; B05C 17/01; B05C 17/015; B65D 83/005; B65D 83/0011; B65D 2583/005; F16N 3/12; G01F 11/026; A61M 11/007; A61M 15/06; A24F 42/00
See application file for complete search history.

(56) References Cited

U.S. PATENT DOCUMENTS

| 2,052,296 | A | 8/1936 | James |
| 2,199,877 | A | 5/1940 | Jose |
| 4,136,801 | A | 1/1979 | Pavenick |
| 6,474,891 | B1 * | 11/2002 | Liu .......................... B43K 8/04 401/172 |
| 8,511,323 | B2 * | 8/2013 | Jimenez ............. A46B 11/0031 401/175 |
| 8,540,124 | B2 | 9/2013 | Francavilla |
| 9,717,859 | B2 | 8/2017 | Harms et al. |
| 9,914,580 | B1 | 3/2018 | Siciliano et al. |

(Continued)

FOREIGN PATENT DOCUMENTS

GB 720860 A * 12/1954

*Primary Examiner* — Donnell A Long
(74) *Attorney, Agent, or Firm* — Kubota & Basol LLP

(57) ABSTRACT

The present invention surrounds a dispenser and means for dispensing viscous fluids, such as those associated with cannabis extracted compounds. More particularly, the dispenser of the present invention is a one-handed controlled dispenser device for viscous fluids with a replaceable cartridge to allow a user to selectively install and use different cartridges containing different fluids as desired or as needed.

19 Claims, 7 Drawing Sheets

(56) References Cited

U.S. PATENT DOCUMENTS

| | | |
|---|---|---|
| 10,329,075 B2 | 6/2019 | Gershoni et al. |
| 10,888,117 B2 | 1/2021 | Danek |
| 10,919,685 B2 * | 2/2021 | Phipps ............... B65D 83/0022 |
| 11,872,587 B2 * | 1/2024 | Bodenmüller .... B05C 17/00576 |
| 2004/0199117 A1 | 10/2004 | Giambattista et al. |
| 2004/0260247 A1 | 12/2004 | Veasey et al. |
| 2005/0283115 A1 | 12/2005 | Giambattista et al. |
| 2007/0016142 A1 | 1/2007 | Burren et al. |
| 2007/0244436 A1 | 10/2007 | Saiki |
| 2008/0306446 A1 | 12/2008 | Markussen |
| 2009/0247960 A1 | 10/2009 | Kohlbrenner et al. |
| 2017/0135398 A1 | 5/2017 | Scott et al. |
| 2018/0327173 A1 * | 11/2018 | Gershoni ................. A61J 1/00 |
| 2018/0361066 A1 | 12/2018 | Hacker |
| 2020/0046030 A1 | 2/2020 | Krietzman |
| 2020/0148462 A1 | 5/2020 | Brugger et al. |
| 2020/0290791 A1 | 9/2020 | Jones et al. |

* cited by examiner

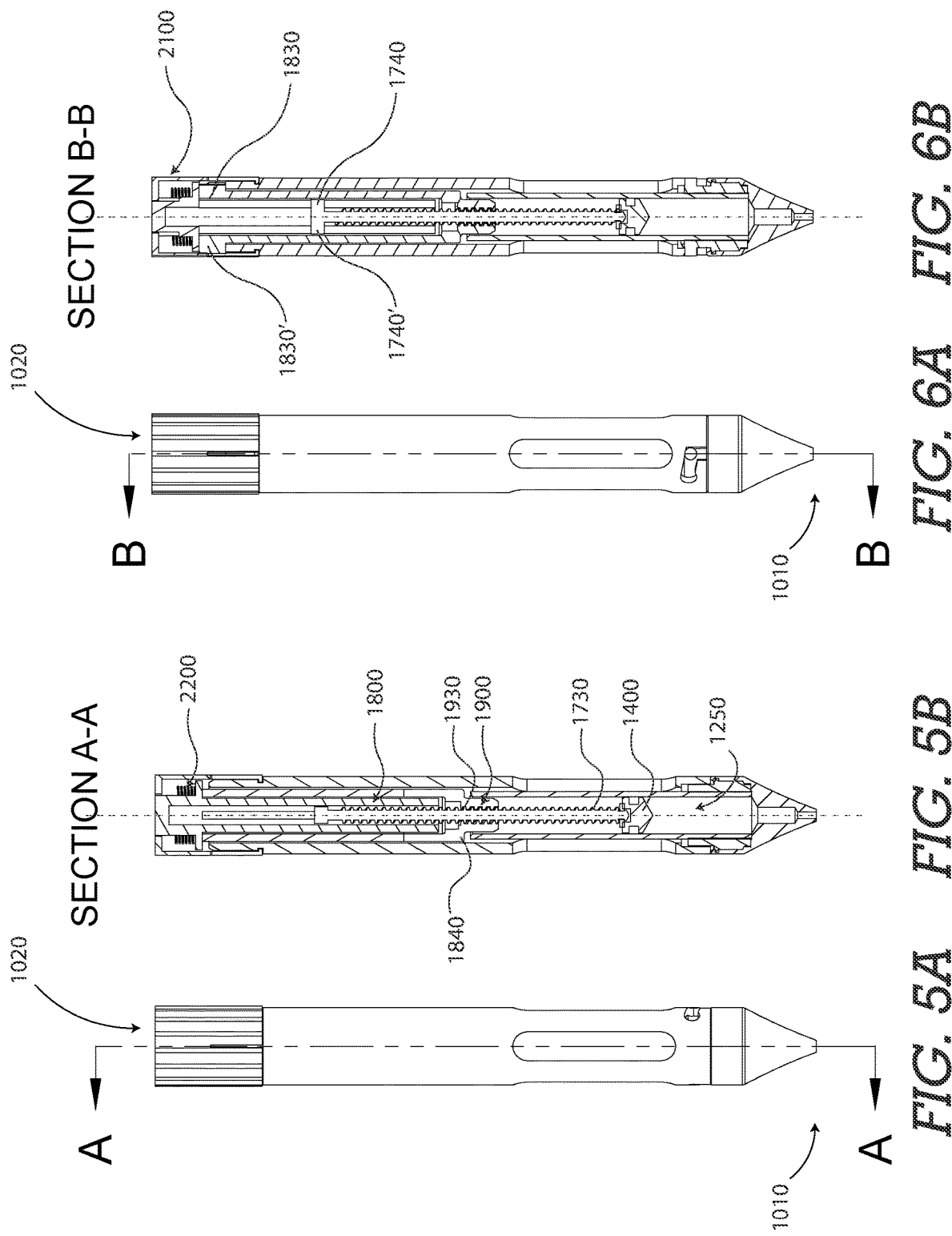

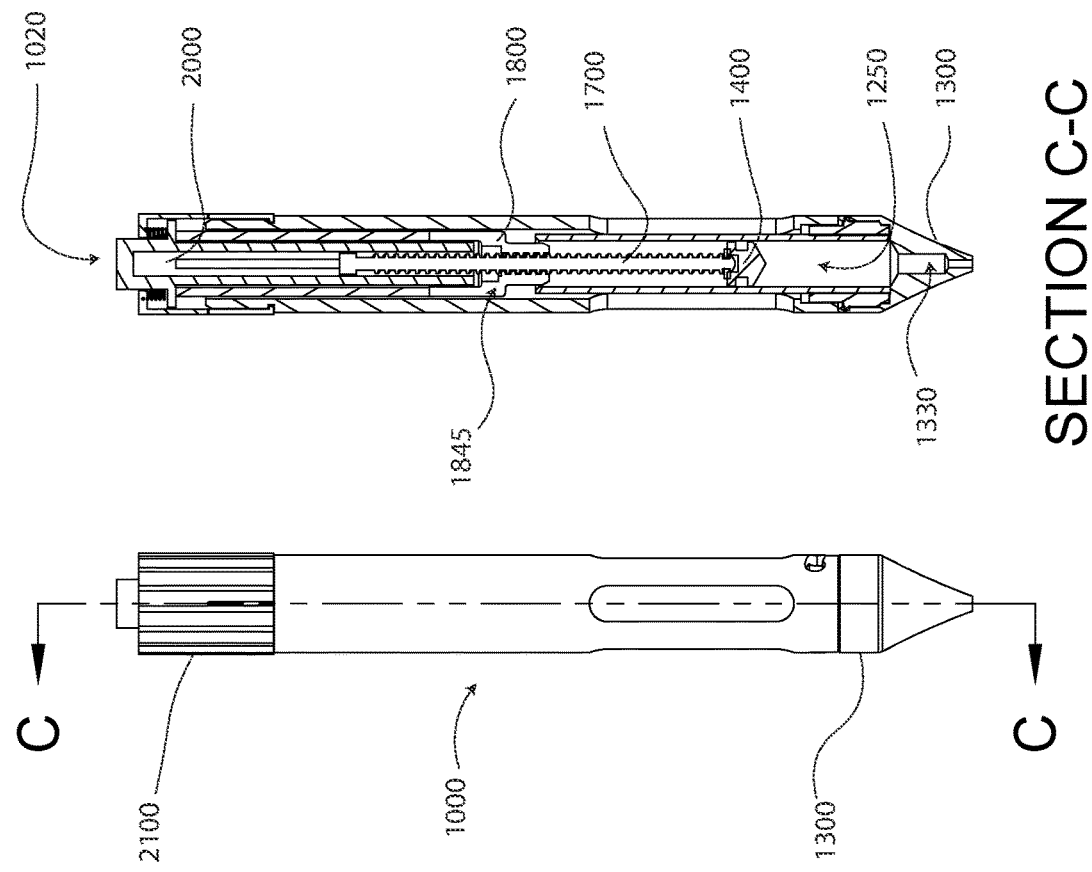
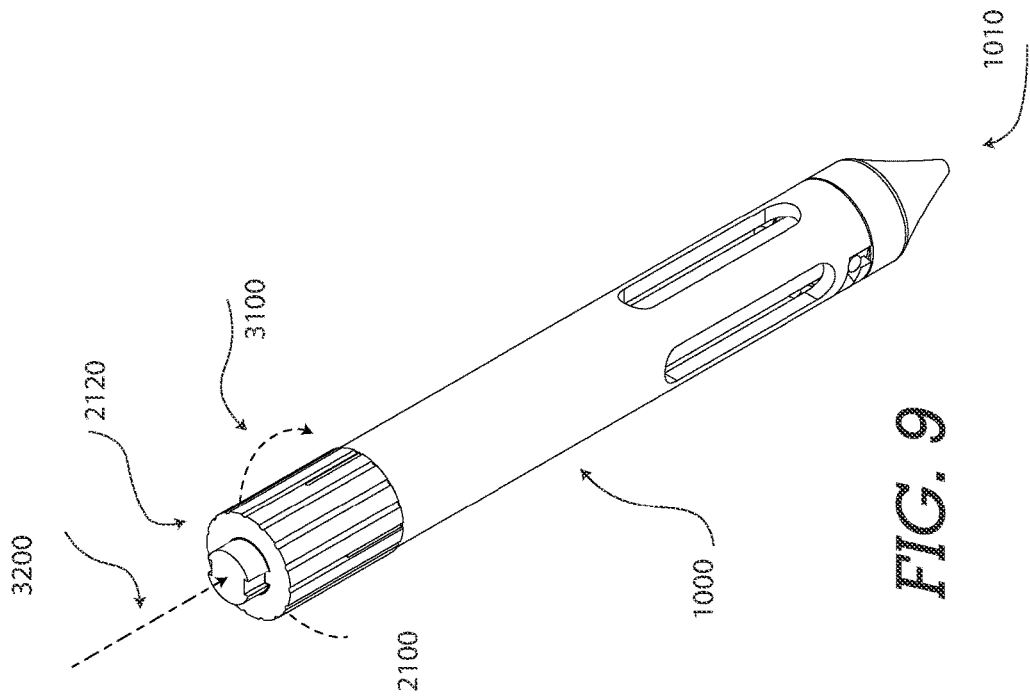

APPARATUS, SYSTEM AND METHOD COMPRISING A DISPENSER WITH A MODULAR CARTRIDGE FOR THE DISPENSING OF CANNABIS EXTRACT

CROSS REFERENCE TO RELATED APPLICATIONS

This application claims the benefit of U.S. Provisional Patent Application 63/232,768 entitled "AN APPARATUS, SYSTEM AND METHOD COMPRISING A DISPENSER WITH A MODULAR CARTRIDGE FOR THE DISPENSING OF CANNABIS EXTRACT" filed on Aug. 13, 2021, the entire contents of which are incorporated herein by reference in its entirety for all purposes.

FIELD OF THE INVENTION

The present invention pertains to a dispenser and means thereof for viscous fluids such as those associated with cannabis extracted compounds. More particularly, the dispenser of the present invention is a one-handed controlled dispenser device for viscous fluids with a replaceable cartridge to allow a user to selectively install and use different cartridges containing different viscous fluids as desired or needed.

BACKGROUND OF THE INVENTION

The use and administration of fluids containing compounds for recreational and medicinal use has increased in recent years, particularly surrounding the use of fluids surrounding cannabis-based extracts, and tobacco-based extracts. These fluids come in many different forms including a low viscosity fluid or tincture, a viscous fluid, or a highly viscous wax like substance. The use of such fluids in the past required the manual transferring of the fluid from a storage container to a system which vaporizes the fluid.

In certain processes which have come to be known as "dabbing" a user traditionally uses a dentistry-like tool for transferring a wax like substance to an extremely hot object (sometimes referred to as a rig) prior to inhaling the vapors that are produced. In use, a rig may reach temperatures of anywhere up to 537° C. (1000° F.). Others may use a syringe like tool to transfer the concentrate to a preheated object and inhale the vapors that are produced.

The increased mainstream adoption and regulation of cannabis products, psychoactive and non-psychoactive in nature, has given rise consumer products which augments user experience and control over the administration of such fluids. Further due to the increased mainstream adoption and regulation of cannabis-based products, the availability of cannabis-based fluids has increased, providing a user with multiple options of cannabis fluid products. Resultantly, there is a need for a device which allows a user to selectively administer one of many cannabis or tobacco-based fluids from a single dispensing apparatus.

SUMMARY OF THE INVENTION

The present invention as disclosed herein surrounds a dispensing apparatus for fluids with which a user can selectively install a cartridge of their choosing, and dispense a fluid with a single-hand operation without limitation from the dispensing apparatus.

Certain existing solutions such as U.S. Pat. No. 10,329,075 to Gershoni et al. ("Gershoni"), incorporated herein in its entirety for all purposes, provide a single-hand operation dispensing device for the measurable and repeatable dispensing of viscous fluids. Gershoni does not allow for the modular replacement of a cartridge allowing a user to selectively install and dispense a fluid as desired.

Certain existing technologies, such as U.S. Pat. No. 9,914,580 to Siciliano et al. and U.S. Patent Publication No. 2017/0135398 to Scott et al., incorporated herein in their entirety for all purposes, provide a device with the ability to refill a reservoir with a fluid. Such technologies do not account for remaining fluid within the reservoir thereby limiting the use of the dispenser to one fluid. Otherwise, a user risks mixing fluids within the fluid remaining in the reservoir of such technologies.

It is an aspect of the present invention to allow for the interchanging of cartridges allowing a user to interchange cartridges as desired to dispense a particular fluid without risk of mixing fluids.

Certain existing technologies such as those U.S. Patent Publication. No. 2020/0046030 to Krietzman ("Krietzman") and U.S. Patent Publication No. 2018/0361066 to Hacker ("Hacker"), incorporated herein in their entirety for all purposes, disclose interchangeable cartridges for the dispensing of fluids, however Krietzman and Hacker fail to teach beyond the concept of the use of a replaceable cartridge and fail to disclose how the cartridge interconnects with the dispenser.

Certain existing technologies which provide an interchangeable cartridge focused on the delivery of low viscosity fluids such as insulin, such as U.S. Patent Publication No. 2004/0199117 to Giambattista et al. ("Giambattista") and U.S. Pat. No. 9,717,859 to Harms et al. ("Harms"), incorporated herein in their entirety for all purposes. Giambattista and Harms teach the use of an interchangeable cartridge configured to be filled with, contain, and dispense fluids having a viscosity similar to that of water 0.8-1.2 mPa·s. Such fluids allow the user to orient the dispenser in a manner which immediately prevents the dispensing of air pockets and the low viscosity nature of such fluids allow the filling of such cartridges may be performed through the small aperture configured for dispensing the fluid. In the case of high viscosity fluids, it is difficult to fill a cartridge through a smaller aperture in the dispensing end configured for dispensing, and filling the cartridge from the plunger end of the cartridge potentially creates large inclusions of air pockets within the fluid which results in inconsistent dispensing of the fluid, wherein the air pockets are not easily removed from the cartridge without further processes.

It is an aspect of certain embodiments of the present invention to provide filling access through the first end of an interchangeable cartridge—the end through which the fluid is dispensed—prior to interconnecting the dispensing tip with the chamber which holds the fluid. Filling a chamber from the dispensing end prior to interconnected the dispensing tip allows the filling of the chamber wherein the chamber can be filled with the dispensing end of the interchangeable cartridge directed upward, and the dispensing tip interconnected thereafter. This allows the filling of the highly viscous fluid in a heated state to lower viscosity while preventing spillage, and prevents entrained air pockets between the fluid and the plunger tip which may otherwise result inconsistent performance when dispensing.

Certain embodiments of the present invention comprise a glass chamber, a polymeric cuff, and a metal dispensing tip. The polymeric cuff provides the ability to mechanically affix the dispensing tip to the chamber mechanically in a manner which addresses temperature variations and thermal expansion without risking damaging the glass chamber. In the event the tip expands due to higher heat, the cuff is able to maintain the mechanical interconnection between the dispensing tip and the chamber, and in the event the tip contracts due to colder temperatures, the cuff is able to flex and prevent the breaking of the glass chamber. Thus, all aspects of the interchangeable cartridge can be constructed from food-safe materials. Embodiments comprising a dispensing tip comprising metal, ceramic materials, and other food safe or high temperature stable materials are within the spirit and scope of the present invention. Embodiments comprising a cuff comprising a polymeric material including silicone-based polymers, are within the spirit and scope of the present invention. Embodiments of the present invention comprising a chamber, comprising glass or glass-like materials which include polymeric materials such as polypropylene or polycarbonate, are within the spirit and scope of the present invention.

In certain embodiments, a plunger mechanism comprises a lead screw wherein the axial motion of the lead screw acts as a plunger to advance a plunger tip within a cartridge to dispense a fluid held within the cartridge. While embodiments described herein surround the dispensing of a viscous fluid, alternate embodiments which involve the dispensing of alternate fluids such as aqueous solutions, gaseous fluids, and air, are within the spirit and scope of the present invention.

It is an aspect of the present invention wherein the swapping of interchangeable cartridges automatically adjusts the lead screw in the event the lead screw is advanced beyond the location of the plunger tip in the interchangeable cartridge which is inserted. In certain embodiments, the engagement between female threads and the lead screw, which is configured to advance the plunger tip, is configured to slip when pressed until a cartridge is fully interconnected with the dispensing device. Thus, the plunger tip within the interchangeable cartridge pushes the lead screw back toward the second end of the device until the interconnection between the female threaded feature and the lead screw is engaged. In certain embodiments, longitudinal slots on the sides of the female threaded feature allow the female threaded feature to expand, allowing the lead screw to slide therethrough. When the cartridge is fully interconnected with the dispensing apparatus, the second end of the chamber restricts the outward flexion of the female threaded feature, thereby preventing the expansion of the female threaded feature and preventing the sliding of the lead screw therethrough.

These and other advantages will be apparent from the disclosure of the inventions contained herein. The above-described embodiments, objectives, and configurations are neither complete nor exhaustive. As will be appreciated, other embodiments of the invention are possible using, alone or in combination, one or more of the features set forth above or described in detail below. Further, this Summary is neither intended nor should it be construed as being representative of the full extent and scope of the present invention. The present invention is set forth in various levels of detail in this Summary, as well as in the attached drawings and the detailed description below, and no limitation as to the scope of the present invention is intended to either the inclusion or non-inclusion of elements, components, etc. in this Summary. Additional aspects of the present invention will become more readily apparent from the detailed description, particularly when taken together with the drawings, and the claims provided herein.

DETAILED DESCRIPTION OF VARIOUS EMBODIMENTS

Certain embodiments of the present invention, as shown in FIG. 1A-FIG. 2B, comprise a dispensing apparatus 1000 for dispensing fluid which comprises a removably interchangeable cartridge 1100. The dispensing apparatus 1000 comprises a first end 1010 and a second end 1020, comprises an outer sleeve 1500 surrounding internal components 1050 of the dispensing apparatus. The outer sleeve 1500 comprises a hollow form for enclosing internal components 1050 of the dispensing apparatus, wherein the internal components 1050 are configured for the dispensing of a fluid. Certain embodiments comprise a cartridge 1100 which slidably interconnects with the first end 1010 of the dispensing apparatus. In certain embodiments, the cartridge 1100 is configured to be slidably interconnected with the first end 1510 of the outer sleeve. The cartridge comprises a chamber 1200, a dispensing tip 1300, and a plunger tip 1400.

Figure 1A:
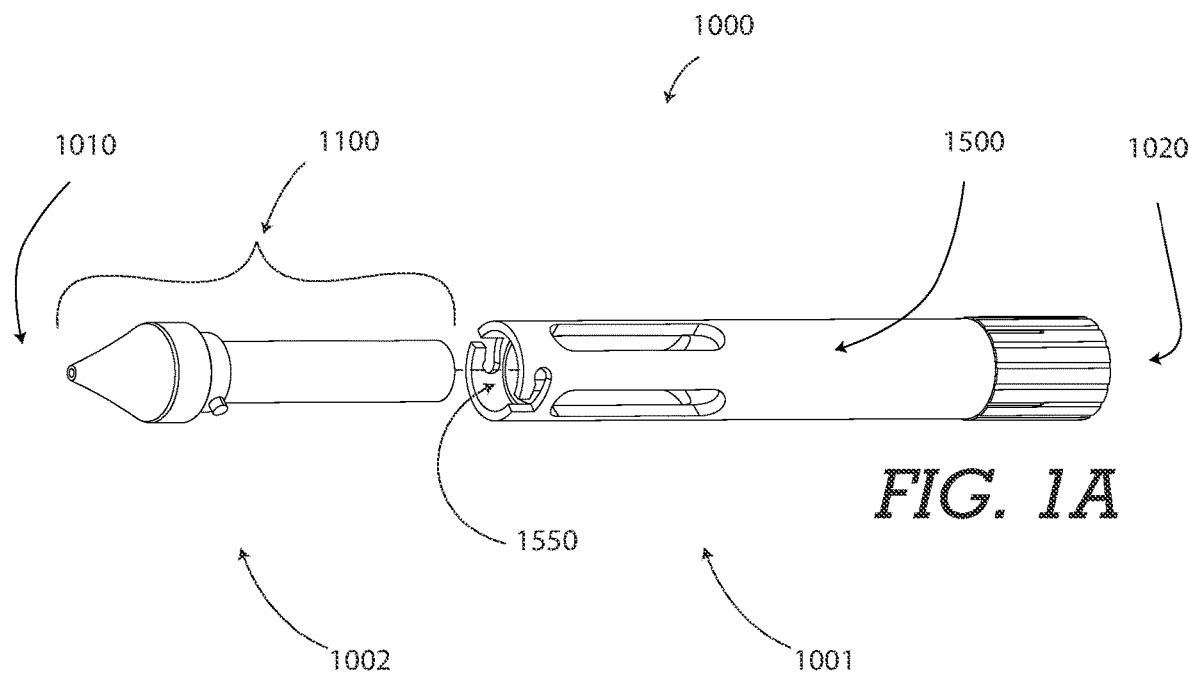
FIG. 1A—A side exploded view of certain embodiments of a dispensing apparatus
Figure 1B:
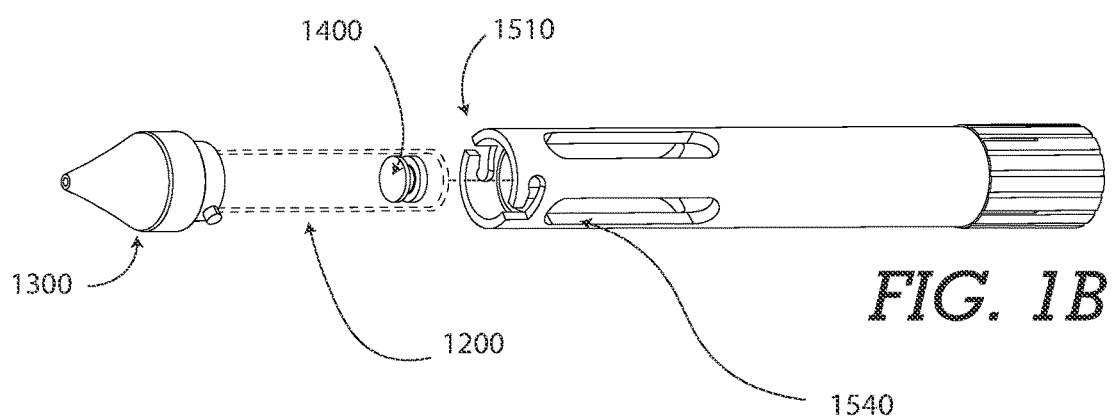
FIG. 1B—The dispensing apparatus of FIG. 1A wherein the chamber is shown in a transparent mode FIG. 2—An exploded perspective view of certain embodiments of a dispensing apparatus FIG. 3A—A perspective exploded view of an interchangeable cartridge FIG. 3B—A perspective exploded view of an interchangeable cartridge FIG. 4A—A perspective view of a dispensing apparatus showing a bayonet mount in an unlocked configuration FIG. 4B—A perspective view of a dispensing apparatus showing a bayonet mount in a locked configuration FIG. 5A—A side view of certain embodiments of a dispensing apparatus FIG. 5B—A cross-sectional view of certain embodiments of the dispensing apparatus of FIG. 5A FIG. 6A—A side view of the dispensing apparatus of FIG. 5A orthogonal to the view of FIG. 5A FIG. 6B—A cross-sectional view of certain embodiments of the dispensing apparatus of FIG. 6A FIG. 7—An exploded side view of certain embodiments of a dispensing apparatus FIG. 8A—A top perspective view of certain embodiments of a dispensing apparatus FIG. 8B—A top view of the dispensing apparatus seen in FIG. 8A FIG. 9—A top perspective view of certain embodiments of a dispensing apparatus FIG. 10A—A side view of certain embodiments of a dispensing apparatus FIG. 10B—A cross-sectional view of certain embodiments of the dispensing apparatus of FIG. 10A
Figure 2:
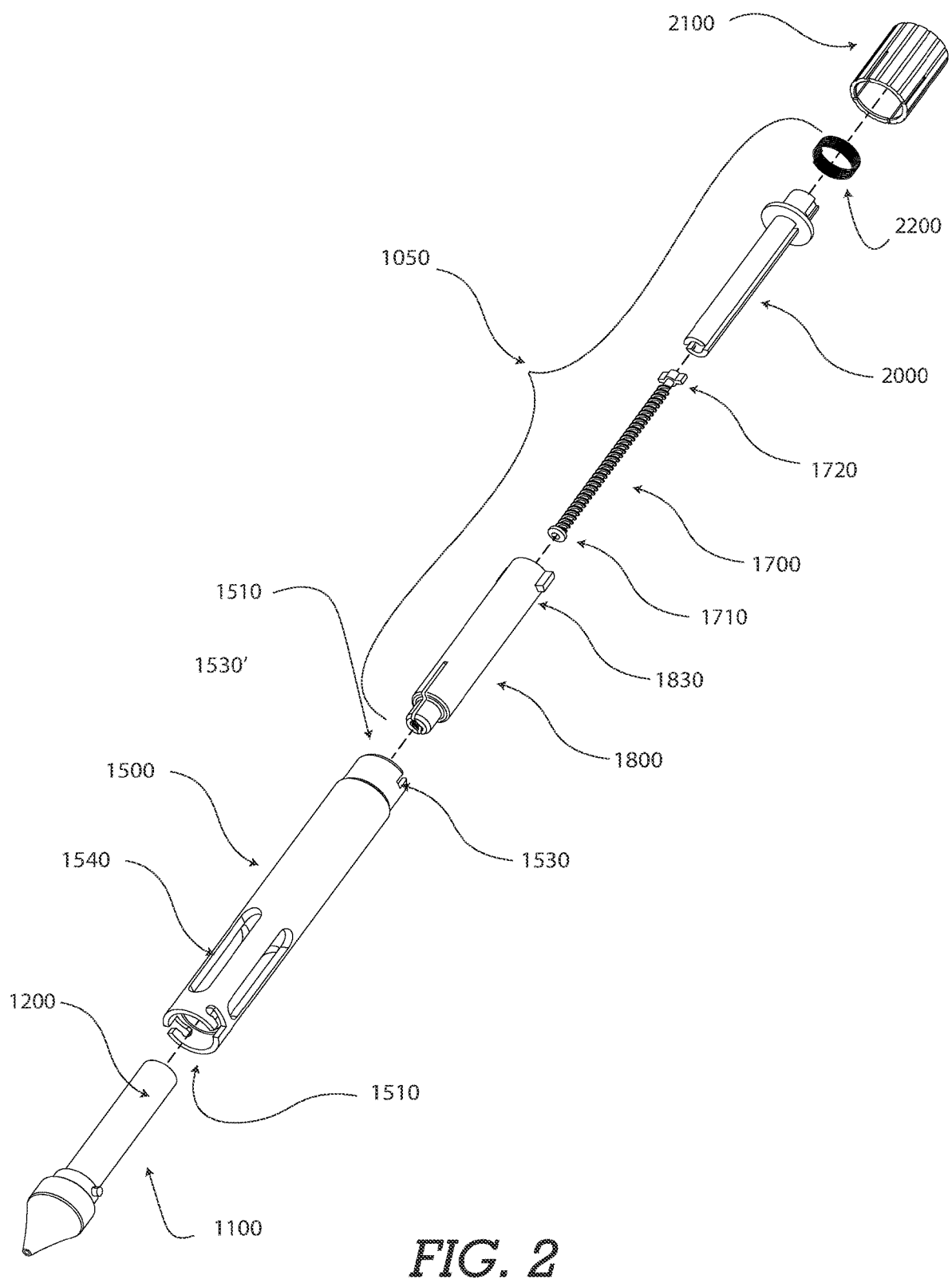
Figure 3A:
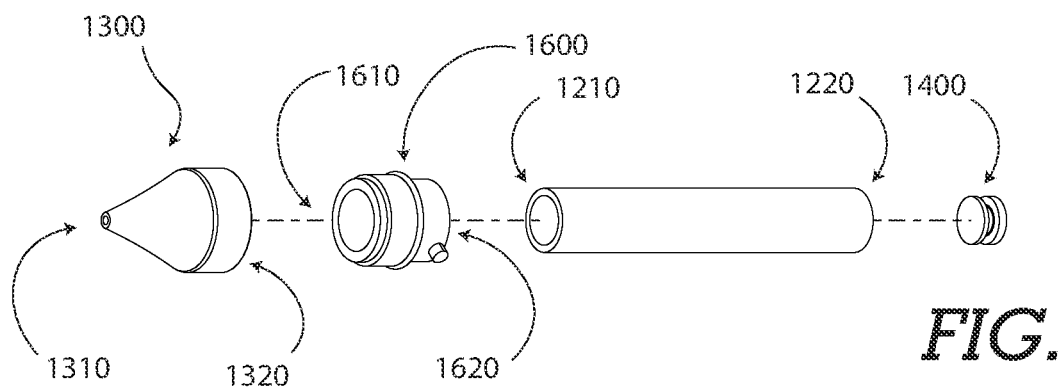
Figure 3B:
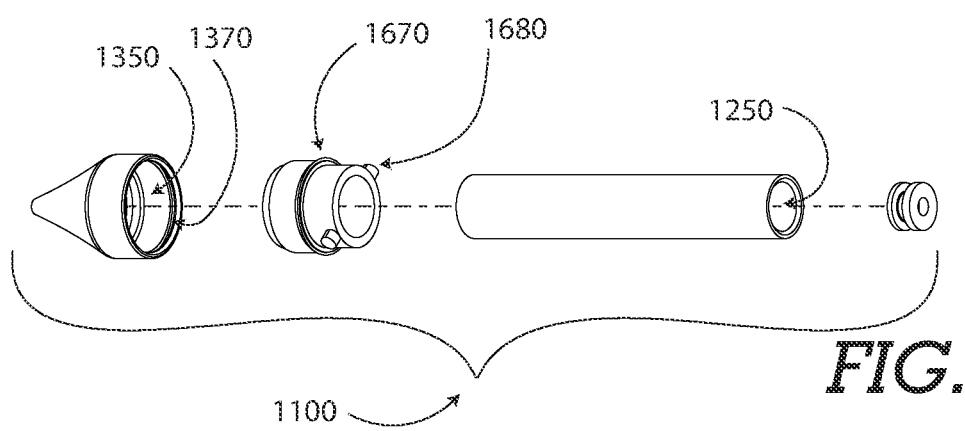
Figure 4A:
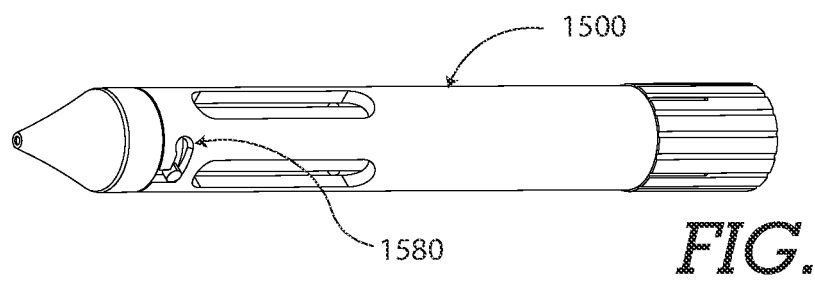
Figure 4B:
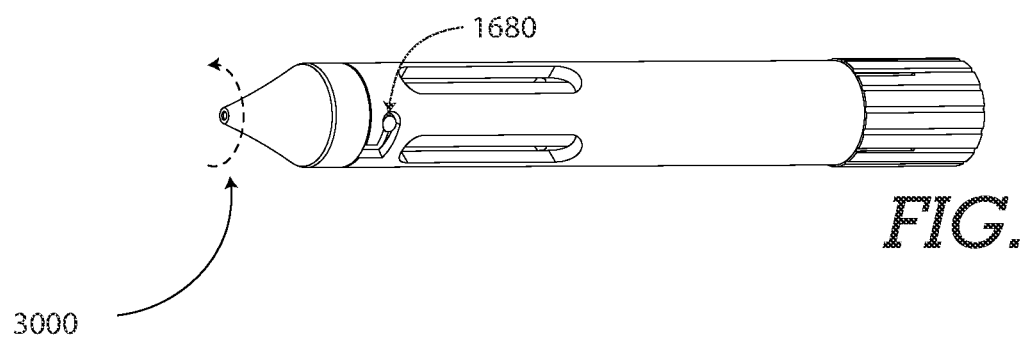
Figure 7:
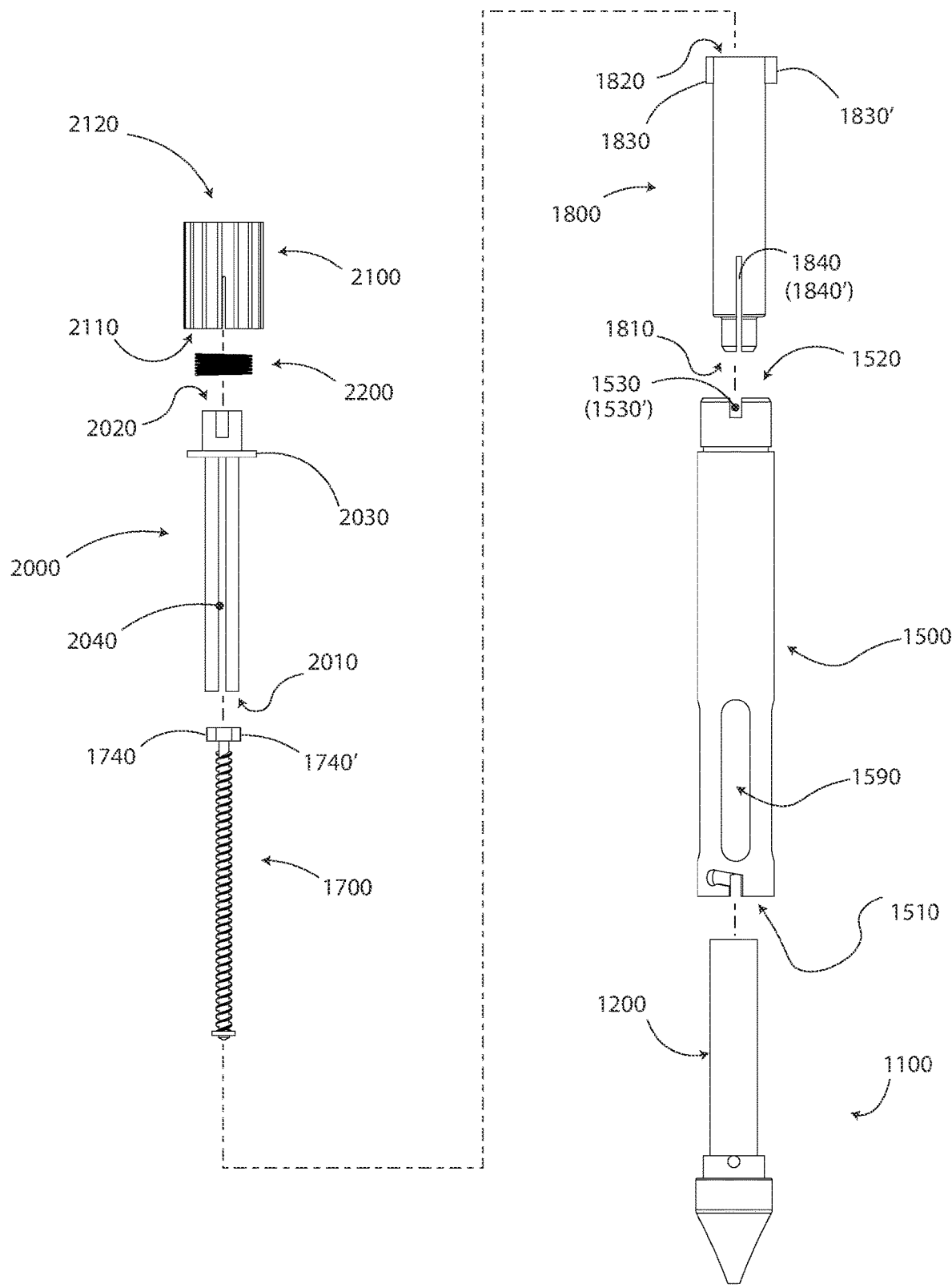

As shown in FIG. 3A-FIG. 3B, the chamber 1200, which is adapted for holding a fluid therein, has an internal bore 1250 which the plunger tip 1400 is configured to have an interference fit therewithin, and the plunger tip 1400 is configured to be advanced toward the first end 1210 of the chamber from the second end 1220 of the chamber. The dispensing tip 1300 which interconnects with the first end 1210 of the chamber, comprises a first end 1310 for dispensing of fluid, and a second end 1320 of the dispensing tip which is configured to interconnect with the first end 1210 of the chamber. In certain embodiments, the second end 1320 of the tip comprises an internal bore 1350 configured to receive the first end 1210 of the chamber therewithin for interconnecting the dispensing tip 1300 with the chamber 1200.

In certain embodiments, a cuff 1600 is disposed between the dispensing tip 1300 and chamber 1200 wherein the second end 1620 of the cuff is configured to have an interference fit around the first end 1210 of the chamber, and a first end of the cuff 1610 is configured to have an interference fit within the internal bore 1350 of the second end of the dispensing tip. In certain embodiments, the outer surface of the cuff comprises a retention feature 1670 configured to interconnect with a retention feature 1370 on the internal bore of second end of the tip, whereby the mating of the retention features 1370,1670 restricts the removal of the dispensing tip 1300 from the cuff 1600 after they have been interconnected. In certain embodiments, the retention features 1370,1670 are configured to snap-fit when interconnected. In certain embodiments the retention features 1370,1670 are configured as mechanical stops wherein the retention features 1370,1670 prevent the over-insertion of the first end 1610 of the cuff into the second end 1320 of the dispensing tip. The second end 1620 of the cuff is configured to slide within the bore 1550 of the outer sleeve, thereby allowing the cartridge 1100 to be slidably interconnected with the first end 1510 of the outer sleeve.

In certain embodiments of the present invention, as shown for instance in FIG. 3A-FIG. 4B, the second end 1620 of the cuff comprises a male bayonet connector 1680 (such as a pin), and the first end 1510 of the outer sleeve comprises a female bayonet connector 1580 (such as a slot) whereby the cartridge can be interlocked to the first end 1510 of the outer sleeve. It will be appreciated that once the male bayonet connector 1680 is inserted within the female bayonet connector, rotating 3000 the cartridge (shown in FIG. 4A-FIG. 4B for instance) indexes the male bayonet 1680 mount within the female bayonet 1580 mount thereby interlocking the cartridge 1100 within the outer sleeve 1500. While embodiments described herein are directed to embodiments comprising a bayonet mount connection between the cartridge and the outer sleeve, alternate embodiment utilizing alternate interconnection mechanisms for the releasable interconnection of the cartridge with the outer sleeve are within the spirit and scope of the present invention. Alternate interconnection mechanisms include, but are not limited to, threaded connections, magnetic connections, electronic connections, and press-fit connections.

In certain embodiments, as shown in FIG. 1A-FIG. 4B for instance, the sleeve 1500 comprises apertures 1540 wherethrough sleeve 1500 wherein a user can view the contents of a cartridge 1100, and the amount of fluid remaining within the chamber 1200 available for dispensing. In certain embodiments of the present invention, the chamber 1200 of the cartridge comprises a transparent or translucent material. While apertures shown herein comprise elongated oblong forms, apertures in alternate embodiments are not restricted thereto, and apertures comprising different shapes are within the spirit and scope of the present invention.

Certain embodiments of the present invention, as shown for instance in FIG. 2 and FIG. 5A-FIG. 6B, comprise a plunger in the form of a lead screw 1700 having a first end 1710 and a second end 1720. The first end 1710 of the lead screw is configured to interconnect with the plunger tip 1400, and is configured to advance the plunger tip 1400 toward the first end 1010 of the dispensing apparatus. The lead screw 1700 comprises male threading 1730 between the first end 1710 and the second end 1720 of the lead screw. In certain embodiments, the lead screw 1700 is also configured to retract the plunger tip 1400 toward the second end 1020 of the dispenser. The plunger tip 1400 of certain embodiments is configured to freely rotate in relation to the lead screw 1700, thereby permitting the rotation of the lead screw 1700 without rotation of the plunger tip 1400.

Certain embodiments of a dispensing apparatus 1000, as shown in FIG. 5A-FIG. 7, comprise an intermediate sleeve 1800 having a hollow cylindrical form configured to slide into and interconnect with the outer sleeve 1500 wherein the first end 1810 of the intermediate sleeve is configured to be inserted through the second end 1520 of the outer sleeve. The second end 1820 of the intermediate sleeve comprises a first key 1830 extending radially outward configured to abut the second end 1520 of the outer sleeve. In certain embodiments the first key 1830 of the intermediate sleeve is configured to interconnect with a keyway 1530 disposed in the second end 1520 of the outer sleeve. Thus, the intermediate sleeve 1800 is unable to slide longitudinally further into the outer sleeve 1500, and the intermediate sleeve 1800 is restricted from rotating in relation to the outer sleeve 1500. In certain embodiments, the intermediate sleeve 1800 comprises a first key 1830 and a second key 1830' interconnected at the second end 1820 of the intermediate sleeve which are 180-degrees offset from each other, and the outer sleeve 1500 comprises a first keyway 1530 and a second keyway 1530' at the second end 1520 of the outer sleeve, wherein the keys of the intermediate sleeve are configured to interconnect with the keyways of the outer sleeve.

In certain embodiments, as shown in FIG. 5A-FIG. 7, the first end 1810 of the intermediate sleeve comprises a female threaded feature 1900 interconnected at the first end 1810 of the intermediate sleeve, wherein the female threaded feature 1900 and the intermediate sleeve 1800 are coaxially aligned. The female threaded feature 1900 comprises threads 1930 configured to interconnect with the threads 1730 of the lead screw, and an external diameter of the female threaded feature 1960 is less than the external diameter 1860 of the intermediate sleeve. The axial rotation of the lead screw 1700 in a first direction in relation to the female threaded feature 1900 results in the longitudinal translation of the lead screw away from the female threaded feature 1900, and the extension of the assembly of the lead screw 1700 and the intermediate sleeve 1800. The axial rotation of the lead screw 1700 in a second direction results in the longitudinal translation of the lead screw 1700 inward toward the female threaded feature 1900, and resulting in the retraction of the assembly of the lead screw 1700 and the intermediate sleeve 1900. In certain embodiments, the intermediate sleeve 1800 further comprises a first slot 1840 extending radially through the wall thickness 1845 (FIG. 10B) of the intermediate sleeve, while alternate embodiments comprise a first slot 1840 and a second slot 1840'. The slots 1840 of the intermediate sleeve extend longitudinally from the first end 1810 of the intermediate sleeve toward the second end 1820 of the intermediate sleeve. The slots 1840 of the intermediate sleeve allow for the female threaded feature 1900 to radially flex outward resulting in disengagement and slippage between the lead screw 1700 and the female threaded feature 1900 wherein the lead screw 1700 can be advanced therethrough without requiring the rotation of the lead screw 1700. The restriction of flexion of the female threaded feature 1900, such as when the second end 1220 of the cartridge is disposed over the first end 1810 of the intermediate sleeve and over at least a portion of the female threaded feature 1900, thereby results in the engagement of the lead screw 1700 with the female threaded feature 1900 thus requiring the rotation of the lead screw 1700 to advance it through the female threaded feature 1900. In certain embodiments, the chamber 1200 comprises a bore 1250 (FIG. 3B) configured to receive the female threaded feature 1900 therewithin, wherein the bore 1250 of the chamber is configured to be disposed over the female threaded feature 1900 thereby restricting the outward flexion of the female threaded feature 1900 thereby engaging the female threaded feature 1900 with the lead screw 1700.

Certain embodiments of a dispensing apparatus comprise an inner sleeve 2000 comprising a hollow cylindrical form, a first end 2010 and a second end 2020. The first end 2010 of the inner sleeve is configured to slidably interconnect with the intermediate sleeve 1800 wherein the second end 1820 of the intermediate sleeve is configured to receive the first end 2010 of the inner sleeve therewithin, wherein the inner sleeve 2000 is configured to be slidably interconnected within the hollow form of the intermediate sleeve 1800. The inner sleeve 2000 further comprises a flange 2030 offset from the second end 2020 of the inner sleeve wherein the flange 2030 is configured to abut the second end 1820 of the intermediate sleeve. Thus, when the inner sleeve 2000 is slidably connected within the intermediate sleeve 1800, the flange 2030 abuts the second end 1820 of the intermediate sleeve preventing further insertion of the inner sleeve 2000 into the intermediate sleeve 1800 and the second end 2020 of the inner sleeve extends outward from the second end 1820 of the intermediate sleeve.

In certain embodiments, the lead screw comprises at least a first key 1740 which is configured to slidably interconnect with a keyway 2040 of the inner sleeve which extends from the first end 2010 of the inner sleeve toward a second end 2020 of the inner sleeve. When the key 1740 of the lead screw is interconnected with the keyway 2040 of the inner sleeve, the lead screw 1700 is permitted to slide longitudinally in relation to the inner sleeve 2000, the lead screw 1700 is restricted from rotating in relation to the inner sleeve 2000. In certain embodiments, the lead screw 1700 comprises a first key 1740 and a second key 1740' disposed 180-degrees from each other, and the inner sleeve 2000 comprises a first keyway 2040 and a second keyway 2040' disposed at 180-degrees from each other, wherein the keys 1740 of the lead screw are configured to slidably interconnect with the keyways 2040 of the inner sleeve.

Figure 8A:
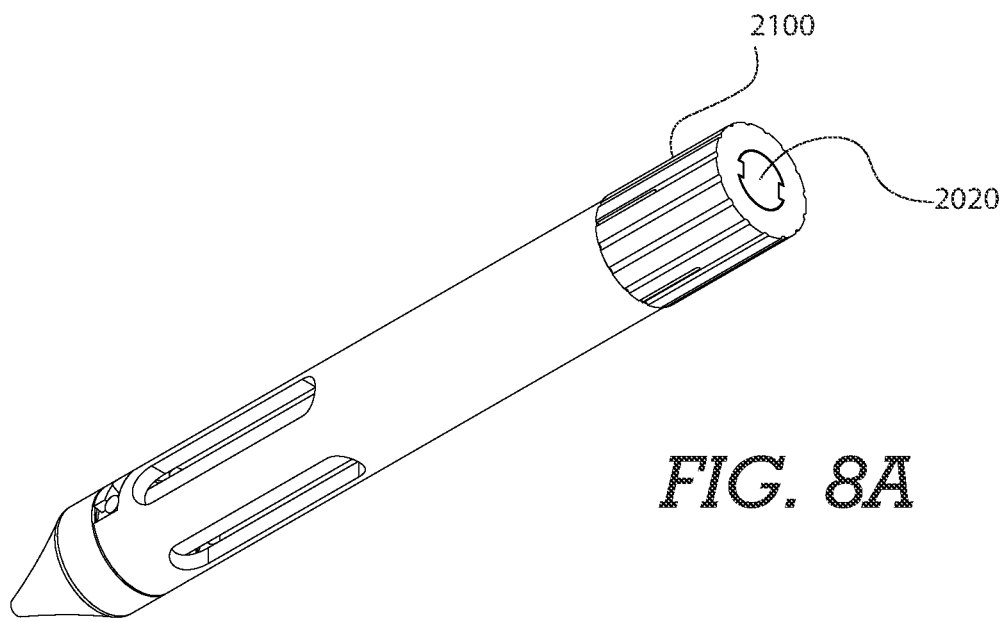
Figure 8B:
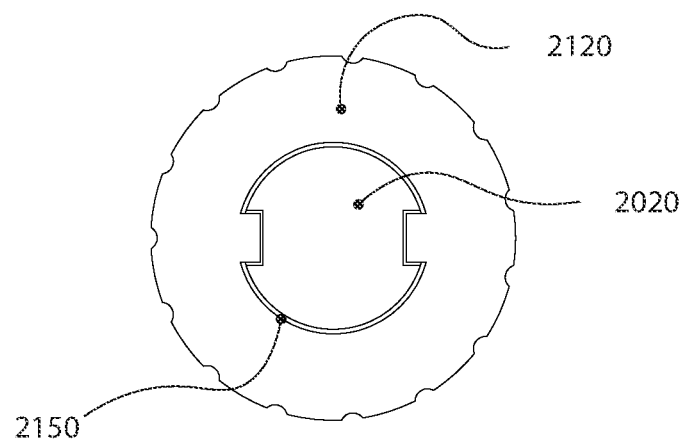

In certain embodiments of the present invention, as shown in FIG. 5A-FIG. 6B, a twisting sleeve 2100 comprises an open first end 2110 configured to interconnect with the second end 1520 of the outer sleeve, wherein the twisting sleeve 2100 is constrained from movement in a longitudinal direction in relation to the outer sleeve 1500, but is permitted to rotate in relation to the outer sleeve 1500. Now referencing FIG. 8A-FIG. 8B, the second end 2120 of twisting sleeve 2100 further comprises a keyed opening 2150 having the same shape as the second end of the inner sleeve 2020, wherein the rotation of the twisting sleeve 2100 results in the rotation of the inner sleeve 2000, and wherein the keyed opening 2150 of the twisting sleeve is configured to permit the sliding of the second end 2020 of the inner sleeve therethrough. In certain embodiments, a spring 2200 (shown in FIG. 5B & FIG. 7) is disposed between the second end of the twisting sleeve 2120 and the flange 2030 of the inner sleeve, wherein the spring 2200 is configured to press the inner sleeve 2100 away from the second end 2120 of the twisting sleeve.

When assembled as described above, and as shown in FIG. 9-FIG. 10B, the dispensing apparatus 1000 provides the ability to dispense a fluid as follows: the rotation 3100 of the twisting sleeve 2100 results in the rotation of the inner sleeve 2000; the rotation of the inner sleeve 2000 results in the rotation of the lead screw 1700; due to the interference fit of the plunger tip 1400 within the chamber bore 1250, the lead screw 1700 remains longitudinally in place and thus results in the translation of the intermediate sleeve 1800 toward the second end 1020 of the dispensing apparatus; the translation of the intermediate sleeve 1800 toward the second end 1020 of the dispensing apparatus results in the extension of the second end 2020 of the inner sleeve through the second end 2120 of the twisting sleeve; and the depressing 3200 of the second end of the inner sleeve translates the inner sleeve 2000 and the intermediate sleeve 1800 longitudinally toward the first end 1010 of the dispensing apparatus; and the translation of the intermediate sleeve 1800 toward the first end 1010 of the dispensing apparatus translates the lead screw 1700 toward the first end 1010 of the apparatus; and the translation of the lead screw 1700 toward the first end 1010 of the apparatus translates results in advancing the plunger tip 1400 toward the first end 1010 of the apparatus, thereby forcing the fluid from the chamber 1200 and through a pathway 1330 of the dispensing tip 1300 of the apparatus.

While various embodiments of the present invention have been described in detail, it is apparent that modifications and alterations of those embodiments will occur to those skilled in the art. However, it is to be expressly understood that such modifications and alterations are within the scope and spirit of the present invention. Further, the inventions described herein are capable of other embodiments and of being practiced or of being carried out in various ways. In addition, it is to be understood that the phraseology and terminology used herein is for the purposes of description and should not be regarded as limiting. The use of "including," "comprising," or "adding" and variations thereof herein are meant to encompass the items listed thereafter and equivalents thereof, as well as, additional items.

What is claimed is:

1. A dispensing apparatus for fluids comprising:
   a first end;
   a second end;
   an outer sleeve having an open first end, and a plunger slidably interconnected within the outer sleeve;
   a cartridge comprising a chamber adapted for containing fluid therein, and a dispensing tip at a first end of the cartridge;
   the dispensing tip comprising a pathway extending therethrough between a first end of the dispensing tip and a second end of the dispensing tip;
   the chamber further comprises a plunger tip slidably interconnected within a bore of the chamber, the plunger tip configured to dispense fluid held within the chamber when the plunger tip is advanced toward the dispensing tip;
   the cartridge is configured to be releasably interconnected with the outer sleeve wherein a second end of the cartridge, is configured to be axially slidably inserted within the open first end of the outer sleeve, and wherein the first end of the cartridge is configured to interlock with the first end of the outer sleeve;
   the plunger further comprises a first end configured to interconnect with the plunger tip when the cartridge is interconnected with the outer sleeve;

an intermediate sleeve slidably connected within the outer sleeve, wherein the intermediate sleeve comprises a female threaded feature; and the plunger comprises a lead screw with threads between the first end of the plunger and the second end of the plunger, wherein the threads are adapted to intermesh with the female threaded feature, wherein:

when the cartridge is interconnected with the outer sleeve, the first end of the plunger is interconnected with the plunger tip, and when a second end of the plunger is depressed toward the first end of the outer sleeve, the plunger tip advances toward the dispensing tip, thereby dispensing the fluid from the chamber, through the pathway, and out of the first end of the dispensing tip, and axial rotation of the lead screw in a first direction in relation to the female threaded feature results in longitudinal extension of the assembled plunger and intermediate sleeve.

2. The dispensing apparatus of claim 1, wherein the female threaded feature is located at the first end of the intermediate sleeve;

the intermediate sleeve further comprises a first slot extending longitudinally from the first end of the intermediate sleeve toward a second end of the intermediate sleeve, the first slot extending radially through a wall thickness of the intermediate sleeve, wherein the first slot is configured to allow the female threaded feature to flex radially outward.

3. The dispensing apparatus of claim 2, wherein when the lead screw is intermeshed with the female threaded feature and the first end of the plunger is depressed toward the second end of the intermediate sleeve, the female threaded feature flexes radially outward, resulting in disengagement between the female threaded feature and the lead screw, thereby allowing retraction of the plunger within the intermediate sleeve without requiring rotation of the plunger in relation to the intermediate sleeve.

4. The dispensing apparatus of claim 3, further comprising a second slot.

5. The dispensing apparatus of claim 2, wherein the bore of the chamber is configured to receive the female threaded feature therein.

6. The dispensing apparatus of claim 5, wherein interconnection of the cartridge with the outer sleeve results in the insertion of the female threaded feature within the bore of the chamber, thereby restricting the female threaded feature from flexing radially outward.

7. The dispensing apparatus of claim 6, wherein the interconnection of the cartridge with the outer sleeve restricts retraction of the plunger within the intermediate sleeve without requiring rotation of the plunger in relation to the intermediate sleeve.

8. The dispensing apparatus of claim 1, wherein the outer sleeve further comprises a first aperture, wherein the first aperture is configured to display contents of the chamber therethrough when the cartridge is interconnected with the outer sleeve.

9. The dispensing apparatus of claim 8, wherein the outer sleeve comprises a plurality of apertures.

10. The dispensing apparatus of claim 1, further comprising an inner sleeve configured to be slidably inserted within the intermediate sleeve;

the inner sleeve is configured to receive the second end of the plunger axially through a first end of the inner sleeve, wherein the plunger and the inner sleeve are rotatively interconnected wherein axial rotation of the inner sleeve in relation to the intermediate sleeve, results in the axial rotation of the lead screw in relation to the female threaded feature.

11. The dispensing apparatus of claim 10, wherein the inner sleeve further comprises a flange offset from a second end of the inner sleeve, wherein the flange is configured to abut the second end of the intermediate sleeve wherein the second end of the inner sleeve extends beyond the second end of the intermediate sleeve.

12. The dispensing apparatus of claim 11, wherein the axial rotation of the inner sleeve in the first direction results in extension of the second end of the inner sleeve from the second end of the dispensing apparatus.

13. The dispensing apparatus of claim 12, wherein the depression of the second end of the inner sleeve results in translation of the inner sleeve toward the first end of the dispensing apparatus, wherein when the cartridge is interconnected with the outer sleeve, the translation of the intermediate sleeve toward the first end of the dispensing apparatus results in the translation of the plunger toward the first end of the dispensing apparatus, wherein the translation of the plunger toward the first end of the dispensing apparatus results in the translation of the plunger tip toward a dispensing tip resulting in the dispensing of the fluid from the dispensing apparatus.

14. The dispensing apparatus of claim 13, further comprising a twisting sleeve; the twisting sleeve interconnected to a second end of the outer sleeve wherein the twisting sleeve is axially constrained, and wherein the twisting sleeve is configured to rotate independently of the outer sleeve; and the twisting sleeve is rotatively constrained with the second end of the inner sleeve, wherein the rotation of the twisting sleeve in the first direction results in the rotation of the inner sleeve in the first direction.

15. The dispensing apparatus of claim 14, further comprising a spring disposed between the twisting sleeve and the flange of the inner sleeve, wherein the spring is configured to press the inner sleeve away from the twisting sleeve and toward the intermediate sleeve.

16. The dispensing apparatus of claim 1, wherein the cartridge further comprises a first bayonet connector; and the first end of the outer sleeve further comprises a second bayonet connector configured to interconnect with the first bayonet connector.

17. The dispensing apparatus of claim 16, wherein the first bayonet connector comprises a male bayonet connector interconnected with a cuff; and the second bayonet connector comprises a female bayonet connector configured to interconnect with the first bayonet connector.

18. The dispensing apparatus of claim 17, wherein the open first end of the outer sleeve is configured to slidably receive the cuff of the cartridge.

19. A dispensing apparatus for the dispensing of fluid comprising:

an inner sleeve having a hollow cylindrical form having a first end and a second end, an intermediate sleeve having a hollow cylindrical form comprising a first end and second end, and an outer sleeve having a hollow cylindrical form comprising a first end and a second end;

the first end of the inner sleeve is configured to be slidably received within the second end of the intermediate sleeve, a flange interconnected to the inner sleeve proximal to and offset from the second end of the inner sleeve is configured to abut the second end of the intermediate sleeve, wherein the inner sleeve is configured to slide into the second end of the intermediate sleeve until the flange abuts the second end of the intermediate sleeve;

the intermediate sleeve comprised configured to be slidably received within the outer sleeve, and a first key and second key extending outward from the second end of the intermediate sleeve, wherein the first end of the intermediate sleeve is configured to slide into the second end of the outer sleeve until the keys of the intermediate sleeve abut the second end of the outer sleeve;

the intermediate sleeve further comprises a female threaded feature interconnected at the first end of the intermediate sleeve, the female threaded feature is coaxial with the intermediate sleeve, wherein the female threaded feature comprises an external diameter less than an external diameter of the intermediate sleeve;

the keys of the intermediate sleeve are 180-degrees opposed, and the second end of the outer sleeve comprise a first keyway and a second keyway, wherein the keys of the intermediate sleeve are configured to slidably interconnect with keyways of the outer sleeve thereby preventing rotation of the intermediate sleeve in relation to the outer sleeve;

the inner sleeve further comprises a first keyway and a second keyway which are 180-degrees opposed, the keyways of the inner sleeve extend from the first end of the inner sleeve toward the second end of the inner sleeve;

a lead screw configured to threadably interconnect with the female threaded feature, the lead screw comprises a first end and a second end, the second end comprises a first key and a second key, wherein the keys of the lead screw are configured to slide within keyways of the intermediate sleeve, and the lead screw comprises a plunger tip at the first end;

the intermediate sleeve further comprises a first slot and a second slot, the slots of the intermediate sleeve extend from the first end of the intermediate sleeve toward the second end of the intermediate sleeve, wherein the slots are 180-degrees opposed;

a chamber comprising a first end, a second end, and a bore, wherein the second end of the chamber is configured to be slidably received within the first end of the outer sleeve, the bore of the chamber is configured to receive the female threaded feature therewithin, and wherein the plunger tip is configured to have an interference fit within the bore of the chamber;

a twisting sleeve having an open first end configured to interconnect with the second end of the outer sleeve, wherein the twisting sleeve is configured to be slidably rotatable about the outer sleeve;

a spring disposed between the second end of the twisting sleeve and the flange of the inner sleeve wherein the spring is configured to press the inner sleeve away from the second end of the twisting sleeve;

a second end of the twisting sleeve comprises a keyed opening having the same shape as the second end of the inner sleeve, wherein the second end of the inner sleeve is configured to slide axially through the keyed opening until the flange of the inner sleeve abuts the second end of the twisting sleeve;

a cuff interconnected around the first end of the chamber, the cuff comprising a retention feature on an exterior surface of the cuff;

a dispensing tip having a first end and a second end, the second end of the dispensing tip is configured comprises a bore configured to receive the first end of the cuff therewithin, the dispensing tip further comprising a retention feature configured to interconnect with the retention feature of the cuff; and the cuff further comprises a male bayonet connector configured to interlock with a female bayonet connector in the first end of the outer sleeve, wherein twisting of the twisting sleeve in a first direction rotates the inner sleeve, thus the inner sleeve rotates the lead screw, thus the female threaded feature translates with the intermediate sleeve toward the second end of the dispensing apparatus, thus the second end of the inner sleeve extends from the second end of the twisting sleeve, wherein pressing the second end of the inner sleeve advances the plunger tip toward the first end of the chamber, thereby dispensing fluid from within the chamber.

* * * * *